US005697363A

United States Patent [19]

Hart

[11] Patent Number: 5,697,363
[45] Date of Patent: Dec. 16, 1997

[54] INHALATION AND MONITORING MASK WITH HEADSET

[75] Inventor: Geoffrey A. Hart, Philadelphia, Pa.

[73] Assignee: Albert Einstein Healthcare Network, Philadelphia, Pa.

[21] Appl. No.: 631,410

[22] Filed: Apr. 12, 1996

[51] Int. Cl.⁶ .......................... A62B 17/04; A62B 18/08; A62B 18/05; A61M 16/00
[52] U.S. Cl. .................. 128/201.24; 128/201.19; 128/203.29; 128/204.22; 128/206.28
[58] Field of Search .................... 128/201.19, 201.24, 128/203.13, 203.14, 203.29, 204.11, 205.25, 206.21, 206.27, 206.28, 207.11

[56] References Cited

U.S. PATENT DOCUMENTS

| 1,391,060 | 9/1921 | Jandron | 128/204.11 |
|---|---|---|---|
| 2,208,633 | 7/1940 | Heidbrink | 128/203.13 |
| 2,625,155 | 1/1953 | Engelder | 128/207.11 |
| 2,814,293 | 11/1957 | Gabb et al. | 128/206.27 |
| 3,347,229 | 10/1967 | Heitman | 128/206.27 |
| 3,850,168 | 11/1974 | Ferguson et al. | 128/206.27 |
| 4,310,307 | 1/1982 | Bellisario | 128/203.29 |
| 5,005,571 | 4/1991 | Dietz | 128/205.25 |

*Primary Examiner*—Kimberly L. Asher
*Attorney, Agent, or Firm*—Titus & McConomy

[57] ABSTRACT

An inhalation/monitoring device is disclosed which has a headpiece adapted to fit a user which include an arcuate support member and ear members which can include a loudspeaker. A face piece is pivotably mounted to the support and includes a fluid chamber positionable over the user's nose for delivery of a gas such as an anesthesia or containing a monitoring device.

12 Claims, 3 Drawing Sheets

INHALATION AND MONITORING MASK WITH HEADSET

FIELD OF THE INVENTION

The present invention relates to an inhalation device for anesthesia administration nebulization, personal respiration protection and like applications and for monitoring exhalation chemistry such as carbon dioxide and, in particular, to a sedation device which provides a non-intrusive mask for administration of anesthesia.

BACKGROUND OF THE INVENTION

Inhalation and breath monitoring devices are generally well known. They include anesthesia masks for the administration of anesthetics such as nitrous oxide and for measuring carbon dioxide, exhalation flow and the like. Also personal respirators used in hazardous environments and personal masks used to filter the air from dust and particulate material. Inhalation devices have also been used for nebulization of various medicines for use in the treatment of various respiratory ailments. Typically such devices have been designed for their specific intended end use. Most often, monitoring means have not been included in an inhalation system.

The use of conscious sedation as a technique in pediatric patient management is now generally recognized and universally accepted. Evidence supports the notion that conscious sedation is an effective management tool for the treatment of painful injury. Such technique utilizes nitrous oxide and oxygen that is available in operating rooms and is becoming available in hospital emergency rooms to administer the anesthetic agent to put the patient into a state of conscious sedation. However, the use of nitrous oxide and oxygen for conscious sedation is not currently prevalent in the management of pediatric trauma patients. There continues to be a problem with the known knowledge and practical clinical efficacy of pediatric anesthesia as a way of controlling anxiety among children. Currently, televisions, videotapes, tape recordings, toys and the like are to be used to calm anxious pediatric patients while administering anesthetic, inhalation or nebulized medicine. Additionally, exhalation monitoring of patients, especially children, is difficult in such circumstances.

A serious problem in the administration of nitrous oxide and oxygen in the emergency room environment is the added anxiety a child undergoes during application of the gas with a mask over its face. This has been found to be true notwithstanding the fact that child's parent may be present at the time of the application. Unfortunately, a very high level of fear is engendered in a child undergoing any medical procedure by covering that child's face with an anesthesia mask. To some extent, this anxiety increases the difficulty of completing the procedure. Accordingly, any method and means of administering inhaled medicines to children is highly desirable. Such devices have been proposed in non-trauma situations, for example a telephone-like apparatus in which prerecorded sound is directed through the handset and anesthesia gas is delivered through the mouth piece, see U.K. Patent Specification GB2081105A. However, in high-stress medical situations a device which facilitates a rapid delivery of anesthetic without requiring a great deal of patient input or control is needed.

It is, therefore, an object of the present invention to provide a pediatric sedation device that interfaces with the child in a non-threatening, non-intrusive manner. It is a further object of the invention to provide a device which is familiar and toy-like to the child and which does not threaten the child even when that child is in a state of medical anxiety. It is a further object of the present invention to provide a mask which is easy to use in a medical situation for pediatric patient management. It is a further object of the invention to provide an inhalation device which is useful not only in the medical environment but which can also be used for other inhalation procedures such as an air filter or personal respirator. It is also an object of the invention to provide a device which can be used to monitor the exhalation chemistry of the user, especially pediatric patients.

SUMMARY OF THE INVENTION

Generally, the present invention relates to an inhalation device which can be used for the delivery of anesthesia, as a nebulizer or a personal respirator and/or can monitor the exhalation chemistry of the wearer. The invention in its simplest form comprises a headpiece adapted to be worn on the user's head and in a preferred embodiment includes an adjustable headset with earpieces housing earphones. The headpiece includes a movable facial element which includes a chamber or mask having an inhalation and exhaust valve associated inlet and exhaust conduits. The inlet conduit can be operably connected to a source of inhalation medicine, a respirator filter or a source of clean air or oxygen. A monitoring device such as $CO_2$ monitor, bourdon gauge, flowmeter, a breathing frequency monitor and like monitoring devices.

In a presently preferred embodiment of the invention, the inhalation device relates to pediatric sedation where it can be used in medical situations without increasing the anxiety of a child in medical distress. Generally, the invention provides a device which the child can place on its head to simulate headphones and a microphone attached thereto.

More specifically, the preferred embodiment provides a headset which is adjustable fit and can over the head of a child of any age. Most importantly, the sedation device of the present invention can be placed on the child by his or herself similarly to a hat. The headset preferably includes a pair of ear pieces which are adapted to cover the ear of the child and can include loudspeakers and integrated circuit chips used to receive and transmit data, pulse oximetry, sound and the like. Pivotally mounted to the ear pieces is an arm or yolk having positioned thereon a facial nose piece adapted to cover the nose of the patient. Integrated into the nose piece is an inhalation and exhalation valve means for delivering anesthesia to the patient and for exhausting exhaled air. In the preferred embodiment of the invention, a pair of gas inlet and exhaust conduits are integrally formed in the pivotable yolk to deliver inhalation medicine or anesthesia to the valve from a source therefor. The exhaust conduit is preferably connected to a small vacuum pump to draw out exhaled air from the user. A monitoring device is most preferably mounted in the exhaust conduit immediately following the valve means.

In another embodiment of the invention a small microphone is included preferably in a mouth piece attached to the pivotable arm separately incorporated as a microphone connected to the electronic circuit chip positioned in the ear piece. Microcircuitry can be included in the headset which activate through LED, infra-red, microwave or other remote control means interactive video or multi-media visual devices used to divert the attention of the user during a medical procedure.

In the preferred embodiment, a communication system, preferably wireless, is included in the circuitry positioned in the headpiece allowing a patient's parents, doctors or the like to communicate and provide assurance or instructions at a close or remote location. The microphone included in the face piece permits the user to remain in constant communication with others to enforce a higher level of assurance and reduce a user's anxiety.

In practice and application, the sedation device of the present invention is made in a variety of attractive colors to provide an easily identifiable and friendly user interface so the child feels very comfortable in placing it on its head. In non-trauma situations or situations where there is not an eminent emergency, it is possible to include a sedation device having the electronic circuits and or the inhalation or exhalation means removed so that the child can become familiar with the device as toy in the waiting room. In such situations, the ear pieces can include a loudspeaker and a closed circuit audio receiver so that when the child places it on its head it will hear music or instructions in the voice of the doctor prior to treatment. Because the sedation device simulates the look and feel of a headphone and microphone as commonly seen by children in use in the broadcast industry it provides a very friendly and non-intrusive method of attaching a child to anesthesia without creating undo anxiety.

Use of the device is typically facilitated by the child's desire to put on the headpiece and simulate the use of headphones. When the child places the headset on its head the pivotable arm and mask are positioned above the head with a microphone thereto. As the child becomes comfortable with the device on its head, the child can rotate the arm or yolk and mask into position in front of his or her nose and mouth. Once in position, the flow of medicine or anesthesia can begin either manually activated by a doctor or automatically by activation of a microswitch positioned in the yolk arm of the sedation device. Normal inhalation and exhalation will continue until the child is in a state of conscious sedation permitting the doctor to commence the procedures that necessitated the visit. The doctor maintains the conscious level of sedation throughout the procedure. By placing the child in a state of conscious sedation the anxiety level created by the medical procedure is significantly reduced and no new anxiety is created by the sedation procedure or the present invention because the device is child friendly. Other advantages of the present invention will become apparent from a perusal of the following detailed description of a presently preferred embodiment taken in connection with the accompanying drawings.

PRESENTLY PREFERRED EMBODIMENT OF THE PRESENT INVENTION

Figure 1:
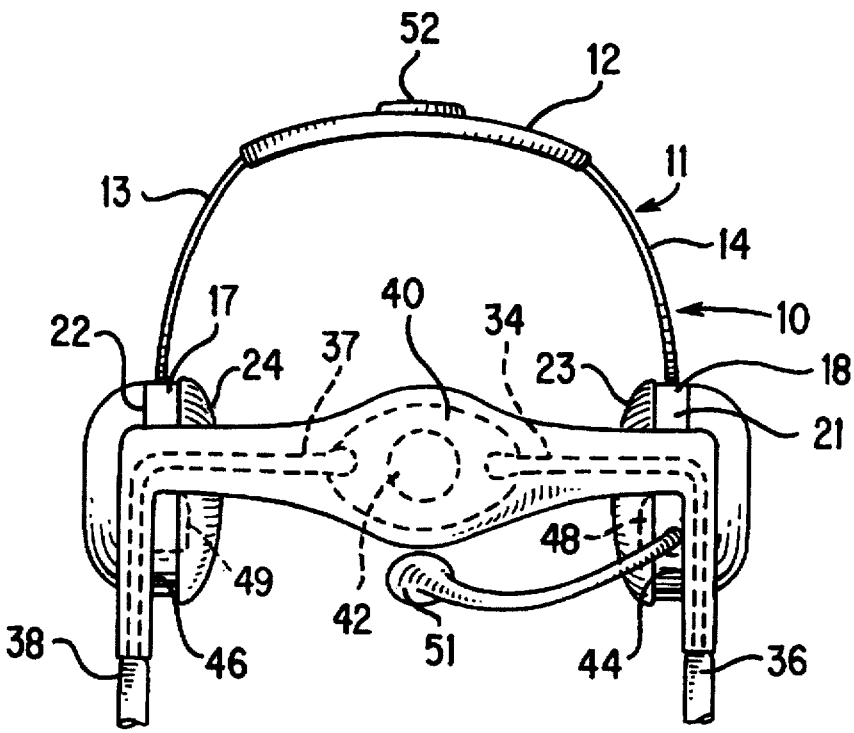
FIG. 1 is a front elevation of the inhalation device of the present invention.
Figure 2:
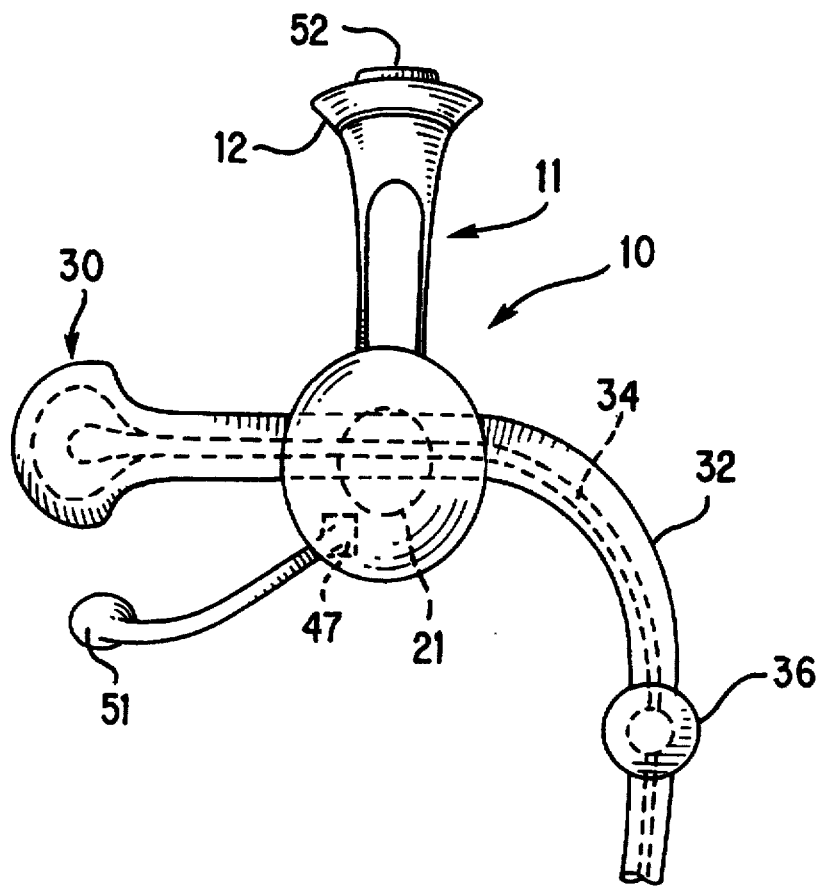
FIG. 2 is a side elevation of a presently preferred embodiment of the invention.

Referring to the drawings, especially FIGS. 1 and 2, inhalation device 10 of the present invention includes a headpiece 11 preferably having a resilient head pad 12 to support sedation device 10 comfortably on the head of a user. Inhalation device 10 will be described hereinafter as it relates to its use as a pediatric sedation device. However, it is to be understood that the device can be used as a nebulizer, respirator or other inhalation means. Headpiece 11 can comprise a pair of head straps 13 and 14 which can be adjustably secured in pad 12. Attached to straps 13 and 14 are ear pieces 17 and 18, respectively.

Ear pieces 17 and 18 are preferably made of a light weight, injection molded polyethylene or polystyrene in the form of an annular disk. This configuration is adapted to support integrated earphones over the ears of a user or can act as sound attenuation means for use in both medical and work environments. Preferably, integrated into ear pieces 17 and 18 are loudspeakers 21 and 22 respectively. Acoustic pads 23 and 24 are shown positioned over the respective ear pieces 17 and 18. The acoustic pads enhance the comfort to the patient or acts as a sound attenuation media.

Figure 4:
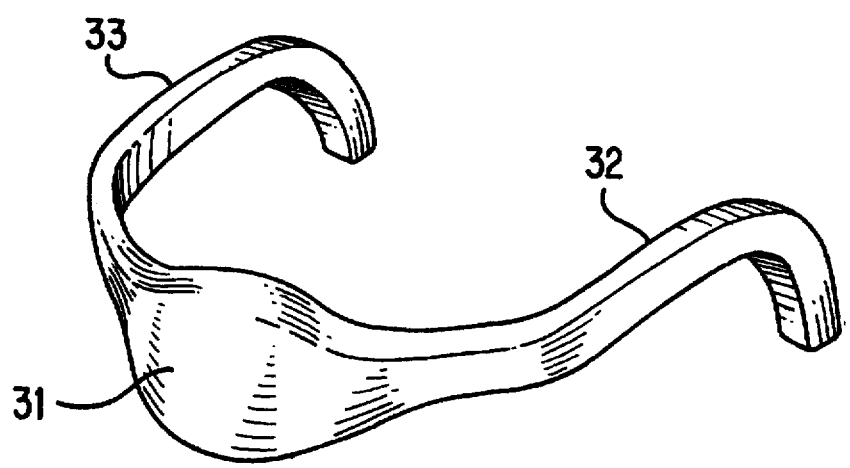
FIG. 4 is a perspective view of another embodiment of the arm and mask integrated into a single unit.

Inhalation device 10 includes a mask member 30 which comprises a face element 31 positionable in front of the nose of the user and a pair of arms 32 and 33, respectively, which form a yolk. In some situations, it may be desirable to use only one of the arms. In the preferred embodiment, face element 31 is integrally molded with arms 32 and 33 to provide a unitary member as shown more specifically in FIG. 4. Incorporated into mask member 30 are fluid inlet conduit 34 and fluid exhaust conduit 37. Inlet conduit 34 is connected to a source of inhalation medicine or anesthesia such nitrous oxide and oxygen and exhaust conduit 37 is vented to the atmosphere or small vacuum pump to ensure removal of exhaled air. In a respirator, inlet conduit can be connected to a respirator filter pack having activated carbon, for example, or a source of clean air or oxygen. Incorporated into face piece 31 is a fluid chamber 40 which has incorporated therein a valve 42 which prevents the inlet fluid, such as anesthetic gas introduced into chamber 40 from escaping into the exhaust conduit 37 during inhalation. However, when the user exhales, valve 42 is removed from its valve seat and exhaust or exhaled gas is permitted to escape from chamber 40 into exhaust conduit 37. Preferably, the use of a gas monitoring device, not shown, is located adjacent to chamber 40 and 42 to monitor the gas exhaled prior to entry into conduit 37.

A number of conventional prior art gas inhalation/exhalation valves may be modified for incorporated into mask 30 of the present invention. Preferably, however, a device such as that shown in U.S. Pat. No. 5,018,519, incorporated by reference herein, is modified and used as the chamber 40. This type of mask is preferred because of its compactness and the efficient design of the exhalation valve incorporated into the facial mask piece 31.

Figure 6:
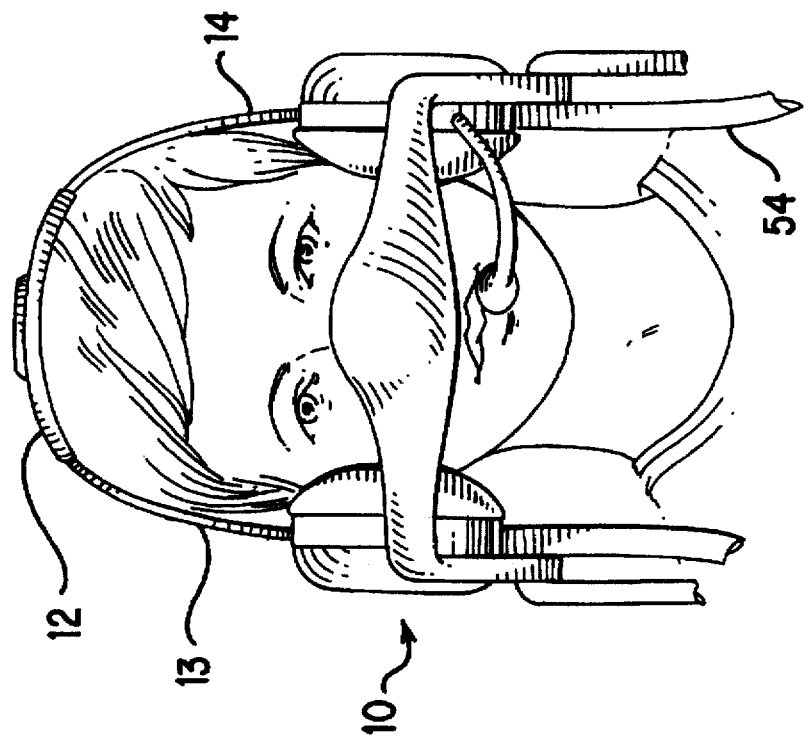
FIGS. 5 and 6 depict the present invention worn by a pediatric patient about to go under sedation.
Figure 5:
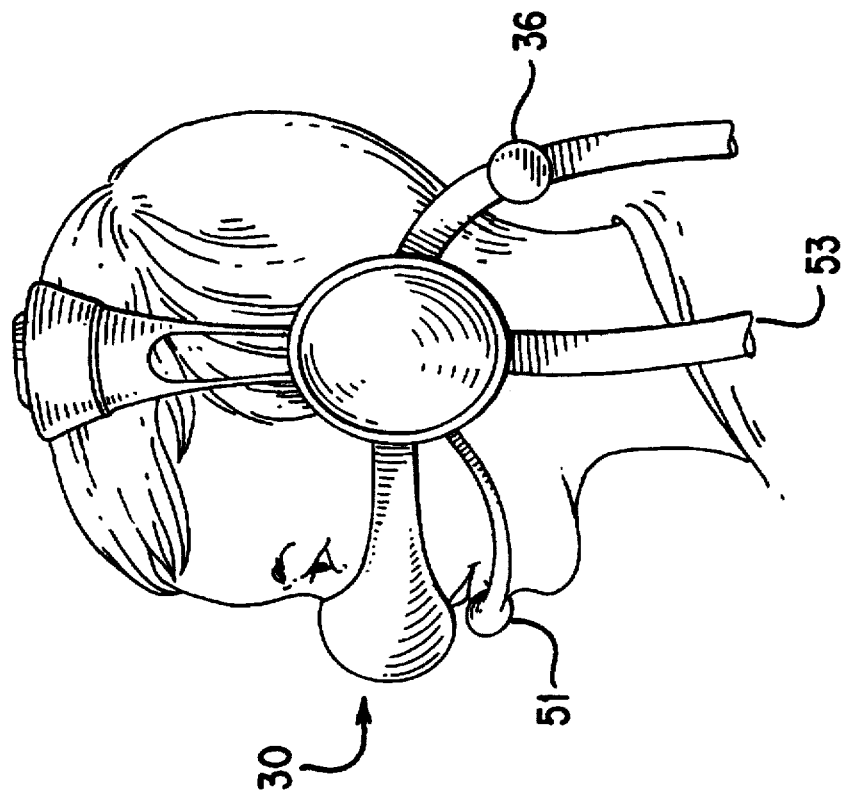

As can be seen in FIGS. 5 and 6, the face piece of the mask 30 is very small in relationship to the face of a user. This permits virtually unobstructed view by the user prior to and during the administration of anesthesia or use of the device. It is particularly advantageous for use as a personal respirator in a work environment. Additionally, device 10 of the present invention stimulates the visual effect and fitness of an audio headset which is particularly useful for application to a pediatric sedation device.

Figure 3:
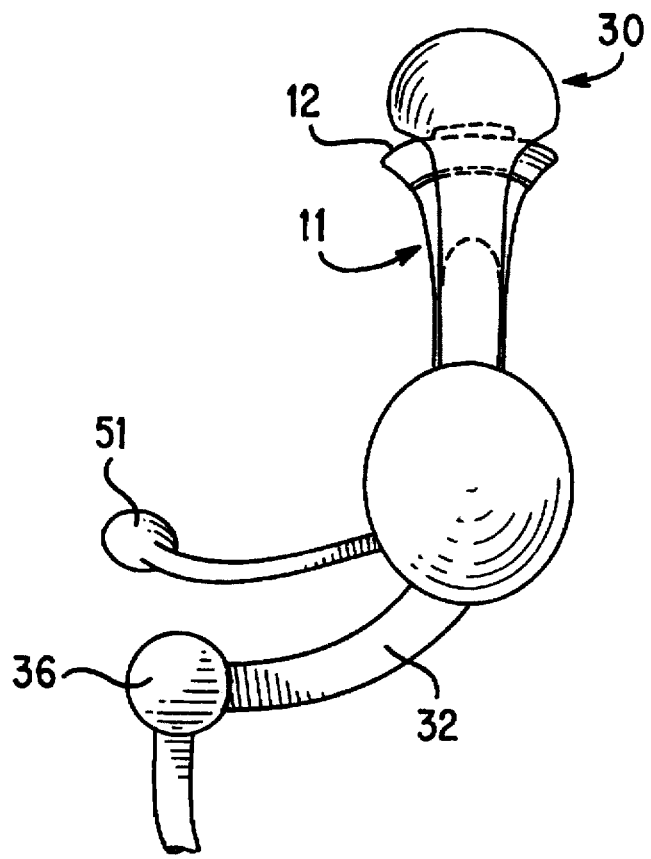
FIG. 3 is a side elevation of the present invention showing the integrated arm and mask in the out-of-use position.

As shown, arms 32 and 33 of mask member 30 form a yolk which is pivotally mounted to ear pieces 17 and 18, respectively, by means of annular pivot flanges 44 and 46, respectively. While any type of rotatable mounting means can be used for this purpose, it is desirable that such mounting provide rotational friction so that mask element 30 can be maintained in the out of use position shown more specifically in FIG. 3. This positioning can also be selectively achieved by using detents to provide fixed locations along the pivot path of mask element 30. Connected to the end of arm 32 is pivot valve 36 used to pivotally connect inlet line 34 with a source of anesthesia, inhalation medicine or a respirator filtration means not shown. Also, pivot valve 38 is included on arm 33 to pivotally connect exhaust conduit 37 with a small vacuum pump, not shown. Pivot valves 36 and 38 facilitate the pivoting of mask element 30 from the out-of-use position of the mask to the in-use position.

In another embodiment of the invention, a small integrated circuit 47 is positioned within one or both ear pieces 17 or 18. Integrated circuit 47 includes receiver and transmitter circuits for communications by and between the user and others. Integrated circuit 47 is electrically connected with speakers 21 and 22 positioned behind acoustic pads 23 and 24, respectively. Also electrically connected to the transmitter circuit of integrated circuit 47 is microphone 51 which is movably positionable to in front of a user's mouth. Also shown on head pad 12 is an infra-red or LED module 52 electrically connected to integrated circuit 47 which can be used to activate an interactive video or other multi-media device to be used to divert patient's attention from the medical procedure or for activating a peripheral device. Interactive devices such as television, audio visuals and the like can be activated by such module. In such other embodiments scanning LEDs can be positioned on face piece element 31 to follow the user's eye movement if they wander away from the video.

In the preferred embodiment, integrated circuit 47 includes its own wireless communication and battery supply packet. However, in order to reduce the initial costs of such unit direct electrical connection is accomplished through external wires 53 and 54 shown on FIGS. 5 and 6, respectively. In such case it is often desirable to include an integrated circuit or circuit means in each of the ear pieces to reduce wiring complication through the headset.

While presently preferred embodiments of the invention have been shown and described in particularity the invention may be otherwise embodied within the scope of the appended claims.

What is claimed is:

1. An inhalation device comprising:
   a. a headset having a substantially arcuate support and at least one piece on an end of said support; and
   b. a mask member having at least one arm member pivotally mounted to said headset, said mask member including a fluid chamber, said fluid chamber having a fluid inlet in communication through said arm member with a source of fluid, an exhaust outlet, and a valve for opening one of said inlet or outlet, said mask member being pivotal to juxtapose said fluid chamber in front of a user's face when said headset is positioned on the head of the user.

2. An inhalation device as set forth in claim 1 wherein said headset includes a pair of ear pieces on respective ends of said support and a second arm member pivotally mounted to said other earpiece.

3. An inhalation device as set forth in claim 2 wherein said pair of arms terminates at and communicates into said fluid chamber, each of said arms being pivotally mounted to an associated ear piece and including at their respective ends a pivot valve for respectively connecting to said source of fluid and exhaust outlet.

4. An inhalation device as set forth in claim 3 wherein said arms each include at least one fluid conduit or exhaust conduit connected to a respective fluid inlet or exhaust outlet, said fluid conduit being connected to a source of fluid through said pivot valve.

5. An inhalation device as set forth in claim 1, 2, 3 or 4 including at least one loudspeaker positioned in at least one of said ear pieces.

6. An inhalation device as set forth in claim 1, 2, 3 or 4 including a loudspeaker positioned in each ear piece and at least one microphone mounted to one of said ear pieces or said mask member and positionable in front of the user's mouth.

7. An inhalation device as set forth in claim 1, 2, 3 or 4 including a receiver and transmitter circuit and a loudspeaker positioned in each ear piece, and a microphone electrically connected to said transmitter circuit.

8. An inhalation device as set forth in claim 1 or 3 including a transmitter circuit and a loudspeaker in at least one of said ear pieces, said transmitter circuit including output means for activating at least an audio or video diversion means.

9. An inhalation device as set forth in claim 1, 2 or 3 wherein said source of fluid comprises an anesthesia for pediatric sedation.

10. An inhalation device as set forth in claims 1, 2 or 3 wherein a monitoring means is positioned in communication with said exhaust outlet.

11. An inhalation device as set forth in claims 1, 2 or 3 wherein a monitoring means is positioned in communication with said fluid inlet.

12. A monitoring device comprising:
   a. a headset having a substantially arcuate support member and at least one ear piece on an end of said support member; and
   b. a mask member having at least one arm member pivotally mounted to said head set and including a fluid chamber for collecting an exhausting exhaled fluid from a user, said fluid chamber having an exhaust port and a monitoring means positioned in communication with said exhaust port.

* * * * *